United States Patent [19]

Daumas et al.

[11] Patent Number: 5,371,233
[45] Date of Patent: Dec. 6, 1994

[54] 2-(TETRAZOL-5-YL)-1,1'-BIPHENYL DERIVATIVES, THEIR PREPARATION AND THEIR USE AS SYNTHETIC INTERMEDIATES

[75] Inventors: Marc Daumas; Christian Hoornaert, both of Paris; Isaac Chekroun, Epinay; Manuel Bedoya-Zurita, Paris; José Ruiz-Montes, Mantes la Jolie; Guy Rossey, Voisins-le-Bretonneux; Héléne Greciet, Val de Reuil, all of France

[73] Assignee: Synthelabo, Le Plessis Robinson, France

[21] Appl. No.: 998,055

[22] Filed: Dec. 29, 1992

[30] Foreign Application Priority Data

Dec. 30, 1991 [FR] France .................................. 91 16290
Mar. 16, 1992 [FR] France .................................. 92 03113

[51] Int. Cl.$^5$ .................. C07D 257/04; C07D 403/10
[52] U.S. Cl. ..................... 548/250; 548/252; 548/253
[58] Field of Search ................. 548/252, 253, 250

[56] References Cited

U.S. PATENT DOCUMENTS

| | | | |
|---|---|---|---|
| 4,820,843 | 4/1989 | Aldrich et al. | 548/252 |
| 4,870,186 | 9/1989 | Aldrich et al. | 548/215 |
| 4,874,867 | 10/1989 | Aldrich et al. | 548/101 |
| 5,039,814 | 8/1991 | Shuman et al. | 548/250 |
| 5,128,355 | 7/1992 | Carini et al. | 514/381 |
| 5,130,439 | 7/1992 | Lo et al. | 548/110 |

FOREIGN PATENT DOCUMENTS 0106140 4/1984 European Pat. Off. .
0449699 10/1991 European Pat. Off. .

OTHER PUBLICATIONS

Journal of the Chemical Society, Perkin Transaction No. 2, No. 12, 1979, London, pp. 1670–1674.

*Primary Examiner*—David B. Springer
*Attorney, Agent, or Firm*—Jacobson, Price, Holman & Stern

[57] ABSTRACT

Compounds corresponding to the formula (I)

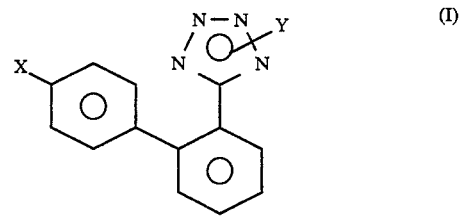

in which X represents dibromomethyl, formyl, $(C_{1-4})$alkyl, or a group $CH(OR_5)_2$ or $CH(OH)OR_5$, wherein the or each $R_5$ is hydrogen $(C_{1-3})$alkyl or the two $R_5$'s in the case of $CH(OR_5)_2$ are linked to provide a 1,3-dioxolane or 1,3-dioxane ring, and Y represents hydrogen, 1,1-dimethylethyl, triphenylmethyl, trimethylstannyl, tributylstannyl, (1,1-dimethylethyl)dimethylsilyl, (1,1-dimethylethyl)diphenylsilyl, 2-cyanoethyl, or a group $CH_2OR_6$ wherein $R_6$ is methyl, phenylmethyl, 1,1-dimethylethyl, 2,2,2-trichloroethyl, benzyloxycarbonyl or 2,2,2-trichloroethyloxycarbonyl, Y being in position 1 or 2 on the tetrazole ring. The compounds of formula (I) are useful as intermediates in the synthesis of compounds possessing therapeutic activity.

13 Claims, No Drawings

2-(TETRAZOL-5-YL)-1,1'-BIPHENYL DERIVATIVES, THEIR PREPARATION AND THEIR USE AS SYNTHETIC INTERMEDIATES

FIELD OF THE INVENTION

The present invention relates to 2-(tetrazol-5-yl)-1,1'-biphenyl derivatives, their preparation and their use as intermediates in the preparation of 3-pyrazolane and 4-pyrimidinone derivatives.

BACKGROUND OF THE INVENTION 1,1'-Biphenyl-4-carboxaldehyde derivatives, corresponding to the formula (1)

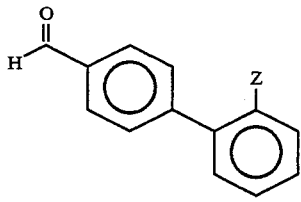

(1)

in which Z is either a cyano group, or a nitro group or an alkoxycarbonyl group, are mentioned in EP-A-0449699.

SUMMARY OF THE INVENTION

The invention provides a compound of the general formula (I)

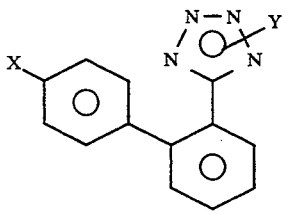

(I)

in which X represents a group selected from dibromomethyl, formyl, $(C_{1-4})$alkyl, a group $CH(OR_5)_2$ and a group $CH(OH)OR_5$, wherein the or each $R_5$ is selected from hydrogen and $(C_{1-3})$alkyl or the two $R_5$'s in the case of $CH(OR_5)_2$ are linked to provide a heterocyclic ring selected from 1,3-dioxolane and 1,3-dioxane, and Y represents an atom or group and selected from hydrogen, 1,1-dimethylethyl, triphenylmethyl, trimethylstannyl, tributylstannyl, (1,1-dimethylethyl)dimethylsilyl, (1,1-dimethylethyl)diphenylsilyl, 2-cyanoethyl and a group $CH_2OR_6$, wherein $R_6$ is a group selected from methyl, phenylmethyl, 1,1-dimethylethyl, 2,2,2-trichloroethyl, benzyloxycarbonyl and 2,2,2-trichloroethyloxycarbonyl, Y being in position 1 or 2 on the tetrazole ring.

DETAILED DESCRIPTION OF THE INVENTION

Preferred compounds of the invention are those wherein X represents a group selected from dibromomethyl, formyl, dimethoxymethyl, 1,3-dioxolan-2-yl and 1,3-dioxan-2-yl, and Y represents an atom or group selected from hydrogen, 1,1-dimethylethyl, triphenylmethyl and methoxymethyl. More preferred compounds of the invention are those wherein X represents a group selected from dibromomethyl and formyl and Y represents an atom or group selected from hydrogen, 1,1-dimethylethyl and triphenylmethyl. Examples of compounds of the invention include 5-(4'-dibromomethyl-1,1'-biphenyl-2-yl)-2-triphenylmethyl-2H-tetrazole, 5-(4'-dibromomethyl-1,1'-biphenyl-2-yl)-2-(1,1-dimethylethyl)-2H-tetrazole, 2'-(2-triphenylmethyl-2H-tetrazol-5-yl)-1,1-biphenyl-4-carboxaldehyde, 2'-[2'-(1,1-dimethylethyl)-2H-tetrazol-5-yl]-1,1'-biphenyl-4-carboxaldehyde, 5-(4'-dimethoxymethyl-1,1'-biphenyl-2-yl)-2-triphenylmethyl-2H-tetrazole, 5-(4'-dimethoxymethyl-1,1'-biphenyl-2-yl)-2-(1,1-dimethylethyl)-2H-tetrazole and 2'-(1H-tetrazol-5-yl)-1,1'-biphenyl-4-carboxaldehyde.

The compounds of the invention can be prepared according to various methods which are well known in organic chemistry. Thus, the aldehydes of formula (Ib) can be synthesised, according to Scheme 1, following one or the other of the reaction sequences, depending on the nature of the substituent Y:

Scheme 1

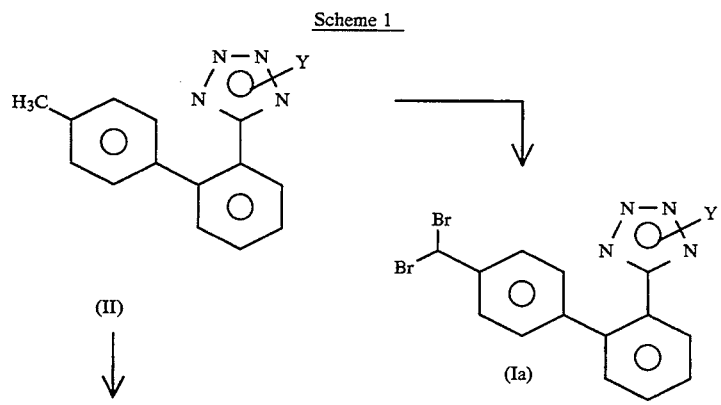

Scheme 1

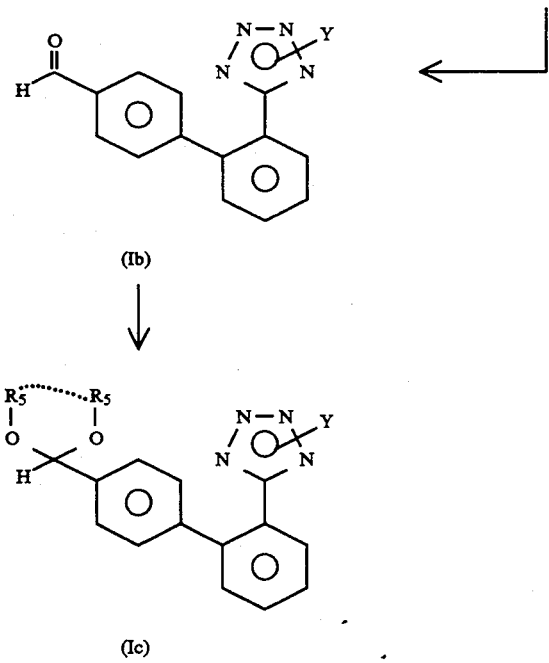

In a first method, a derivative of formula (II) is treated with an oxidising agent, such as, for example, ceric ammonium nitrate or potassium permanganate. Examples of the use of this method will be found in *Synthesis*, 1989, 293 and in *Can. J. Chem.*, 1976, 54, 411. The derivatives of formula (II) in which Y is either a hydrogen atom, or a group $SnR_3$ where R is a $(C_{1-6})$alkyl group or a phenyl group or a cyclohexyl group, or a triphenylmethyl group, or a 2-cyanoethyl group or a (4-nitrophenyl)methyl group are described in European Patent Application EP 0291969.

In a second method, the derivatives of formula (II) are converted to derivatives of formula (Ia), for example by making them react with N-bromosuccinimide, in a solvent such as carbon tetrachloride, in the presence of an initiator such as benzoyl peroxide or $\alpha,\alpha'$-azoisobutyronitrile, at reflux temperature. The derivatives of formula (Ia) are converted to aldehydes of formula (Ib). This conversion can be carried out either by reacting with an amine such as pyridine, hydroxylamine, hydrazine or morpholine and by hydrolysing, or by a hydrolysis catalysed by an organic or inorganic base or acid, or by a hydrolysis catalysed by silver salts, or by a solvolysis in an aliphatic diol or alcohol. Examples of these types of conversions will be found in *J. Labelled Comp.*, 1972, 8, 397; *Syn. Comm.*, 1987, 17, 1695; *Org. Synth.*, 1954, 34, 82; *Tetrahedron Lett.*, 1984, 25, 3099.

The aldehyde functional group of the compounds of formula (Ib) can be protected, for example, in the form of an aliphatic or alicyclic acetal, to give compounds of formula (Ic), in particular 1,3-dioxolanes or 1,3-dioxanes, by using techniques which are well established in organic chemistry and which are described, for example, by T. W. Greene in *Protective Groups in Organic Synthesis*, 1981, Wiley-Interscience.

U.S. Pat. No. 5,039,814 describes a process for the preparation of analogous derivatives, from organolithium compounds, which includes an intermediate stage of transmetallation in the presence of a catalyst.

Another process of the invention makes it possible to carry out a direct aryl-aryl coupling in the presence of a catalyst, according to Scheme 2 below:

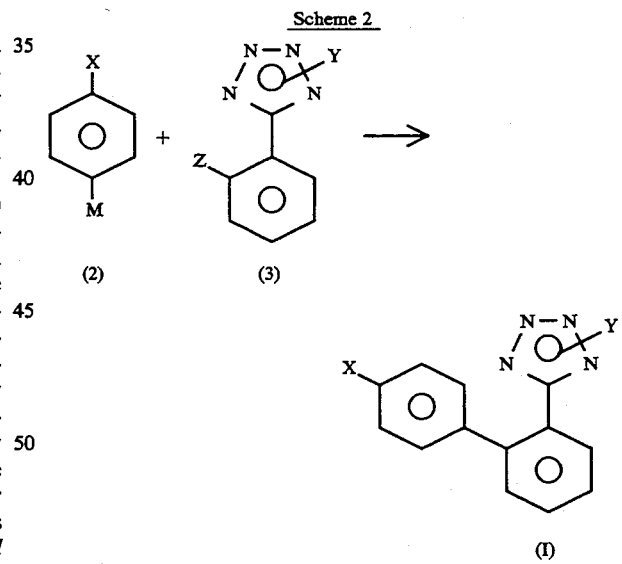

For the compounds of formula (I) in which X does not represent the dibromomethyl group, a coupling between a compound of formula (2), in which M represents a metal chosen from aluminium, boron, cadmium, copper, magnesium and zinc, and a compound of formula (3), in which Y is as defined above and Z represents a bromine or iodine atom, is carried out in the presence of a catalytic quantity of palladium or activated nickel, if necessary, with a Grignard reagent or an aluminium hydride.

The compounds of formula (Ib) can be obtained by hydrolysis of the compounds of formula (I) in which X represents either a group $CH(OR_5)_2$ or a group CH(OH)OR$_5$, R$_5$ being a hydrogen atom or a (C$_{1-3}$)alkyl group which can optionally form, in the case of CH(OR$_5$)$_2$, a 1,3-dioxolane or 1,3-dioxane ring.

The starting compounds are commercially available or are described in the literature or can be prepared according to methods which are described therein or which are known to those skilled in the art.

Thus, the compounds of formula (3) are prepared according to the method described by Z. Grzonka et al., *J. Chem. Soc., Perkin Trans. II*, 1979, 12, 1670–1674.

The following examples illustrate the invention.

Analyses confirm the structures of the compounds.

EXAMPLE 1

5-(4'-Dibromomethyl-1,1'-biphenyl-2-yl)-2-triphenylmethyl-2H-tetrazole.

1.1  5-(4'-Methyl-1,1'-biphenyl-2-yl)-2-triphenylmethyl-2H-tetrazole.

METHOD NO. 1

0.360 g of magnesium in 4 ml of anhydrous tetrahydrofuran are introduced into a 2-necked, round-bottomed flask equipped with a reflux condenser and a dropping funnel. 2 g (11.7 mmol) of 1-bromo-4-methylbenzene in solution in 15 ml of anhydrous tetrahydrofuran are then added dropwise under gentle reflux. The mixture is left to stir for 1 hour at room temperature and then 11.7 ml of a 1M solution of zinc chloride in ethyl ether are added at 0° C. The mixture is left for 30 minutes at room temperature.

The nickel complex is prepared in another round-bottomed flask by treating 0.190 g of dichlorobis(triphenylphosphine)nickel(II), dissolved in 10 ml of anhydrous tetrahydrofuran, with 0.15 ml of a 3M solution of methylmagnesium chloride in tetrahydrofuran. 3 g (5.83 mmol) of 5-(2-iodophenyl)-2-triphenylmethyl-2H-tetrazole in solution in 15 ml of anhydrous tetrahydrofuran are then added. The mixture is stirred for 15 minutes at room temperature and the zinc derivative obtained above is introduced using a transfer needle. The mixture is stirred for 1 hour at room temperature. 20 ml of water are then added, the mixture is extracted with 150 ml of ethyl acetate, the extract is washed with 20 ml of a saturated sodium chloride solution and dried over magnesium sulphate.

The product obtained is purified by chromatography on a column of silica gel by eluting with an ethyl acetate/hexane (¼) mixture.

2.2 g of product are obtained in the form of a white solid.

Melting point = 161°–162° C. Yield = 78.8%

METHOD NO. 2

1 g (1.9 mmol) of 5-(2-iodophenyl)-2-triphenylmethyl-2H-tetrazole, 0.29 g (2.13 mmol) of para-tolueneboronic acid, 60 mg of (dibenzylideneacetone)palladium, 110 mg of triphenylphosphine, 2 ml of a 2M solution of sodium carbonate and 20 ml of toluene are introduced successively into a 2-necked, round-bottomed flask equipped with a reflux condenser. This mixture is maintained at 100° C. for 16 hours. After cooling and separating, the aqueous phase is extracted with 150 ml of ethyl acetate; the organic phases are combined, washed successively with 20 ml of water and with 20 ml of a saturated sodium chloride solution and dried over magnesium sulphate. After evaporating the solvent, the residue is purified by chromatography on a column of silica gel by eluting with an ethyl acetate/hexane (¼) mixture.

0.69 g of product is obtained in the form of a white solid.

Melting point = 161°–162° C. Yield = 74.1%

METHOD NO. 3

0.360 g of magnesium in 4 ml of anhydrous tetrahydrofuran is introduced into a 2-necked, round-bottomed flask equipped with a reflux condenser and a dropping funnel. 2 g (11.7 mmol) of 1-bromo-4-methylbenzene in solution in 10 ml of anhydrous tetrahydrofuran are then added dropwise under gentle reflux. The mixture is left to stir for 1 hour at room temperature.

The palladium complex is prepared in another round-bottomed flask by treating 0.2 g of dichlorobis(triphenylphosphine)palladium(II), dissolved in 10 ml of anhydrous tetrahydrofuran, with 0.6 ml of a 1M solution of diisobutylaluminium hydride in hexane. 3 g (5.8 mmol) of 5-(2-iodophenyl)-2-triphenylmethyl-2H-tetrazole in solution in 15 ml of anhydrous tetrahydrofuran are added to this solution. The mixture is stirred for 15 minutes at room temperature and the magnesium derivative obtained above is introduced using a transfer needle. The mixture is stirred for 1 hour at room temperature. 15 ml of water are then added, the mixture is extracted with 100 ml of ethyl acetate, the extract is washed with 20 ml of a saturated sodium chloride solution and dried over magnesium sulphate.

The product obtained is purified by chromatography on a column of silica gel by eluting with an ethyl acetate/hexane (¼) mixture.

1.6 g of product are obtained in the form of a white solid.

Melting point = 161°–162° C. Yield = 57.3%

1.2  5-(4'-Dibromomethyl-1,1'-biphenyl-2-yl)-2-triphenylmethyl-2H-tetrazole.

5 g (10.5 mmol) of the compound obtained above are dissolved in 60 ml of carbon tetrachloride. 4.1 g (23 mmol) of N-bromosuccinimide and 50 mg (0.304 mmol) of α,α'-azobisisobutyronitrile are added and the mixture is then brought to reflux for 2 hours. The mixture is left to cool and is filtered. The filtrate is evaporated and the residue is triturated under ether. 5.97 g of the expected compound are obtained in the form of a white powder. This compound is subsequently used without purification.

Yield = 89% Melting point = 176° C.

EXAMPLE 2

5-(4'-Dibromomethyl-1,1'-biphenyl-2-yl)-2-(1,1-dimethylethyl)-2H-tetrazole.

2.1  5-(4'-Methyl-1,1'-biphenyl-2-yl)-2-(1,1-dimethylethyl)-2H-tetrazole.

2.3 g (8.8 mmol) of 5-(4'-methyl-1,1'-biphenyl-2-yl)-1H-tetrazole are dissolved in 10 ml of trifluoroacetic acid, and 0.86 g (8.8 mmol) of 95% sulphuric acid and 1.3 g (18 mmol) of tert-butanol, dissolved in 2 ml of dichloromethane, are added. The mixture is stirred for 5 hours at room temperature. The reaction mixture is poured into 120 ml of ice-cooled water and is extracted with 2 times 80 ml of dichloromethane. The organic phase is washed with 50 ml of a saturated sodium bicarbonate solution. The organic phase is dried over magnesium sulphate. The solvent is evaporated to give 2.82 g of the expected compound in the form of an oil which solidifies. The crude product is subsequently used as it is. By crystallising from an ethanol/water mixture, the product is obtained in the form of a white powder.

Quantitative yield Melting point=93°–95° C.

2.2   5-(4'-Dibromomethyl-1,1'-biphenyl-2-yl)-2-(1,1-dimethylethyl)-2H-tetrazole.

Following Example 1.2, from 2.2 g (7.5 mmol) of the compound obtained above, an oil is obtained which is chromatographed on a column of silica gel by eluting with a dichloromethane/cyclohexane mixture. The purified oil is triturated in pentane and 1.57 g of the expected compound are obtained in the form of a white powder.

Yield=46% Melting point=92°–94° C.

EXAMPLE 3

2'-(2-Triphenylmethyl-2H-tetrazol-5-yl)-1,1'-biphenyl-4-carboxaldehyde.

5.4 g (7.2 mmol) of the compound obtained in 1.2 are suspended in a mixture containing 100 ml of acetonitrile and 10 ml of dimethylformamide. 4.18 g (15 mmol) of silver carbonate are added and the mixture is heated at reflux for 7 hours. The mixture is diluted with 100 ml of dichloromethane and the precipitate is filtered. The solvent is evaporated. The crude product is taken up in 150 ml of dichloromethane and washed with 2×50 ml of a 0.5M potassium carbonate solution, then with 50 ml of water, then with 50 ml of 0.1N hydrochloric acid and finally with 50 ml of water. The organic phase is dried over magnesium sulphate and the solvent is evaporated. The oil obtained is purified by chromatography on a column of silica gel by eluting with a dichloromethane/cyclohexane gradient. A colourless gum is obtained which is triturated in ether. 1.4 g of the expected compound are obtained in the form of a white powder.

Yield=40% Melting point=157°–158° C.

EXAMPLE 4

2'-[2'-(1,1-Dimethylethyl)-2H-tetrazol-5-yl]-1,1'-biphenyl-4-carboxaldehyde.

From 1.2 g (2.7 mmol) of the compound obtained in 2.2, following the procedure described in Example 3, 0.8 g of the expected compound is obtained in the form of an oil. It is purified by chromatography on a column of silica gel by eluting with dichloromethane. The purified oil is triturated in pentane and 0.59 g of product is obtained in the form of a white powder. After recrystallising from an ethanol/water mixture, the product is obtained in the form of white crystals.

Yield=72% Melting point=64°–67° C.

This compound can also be obtained by heating 0.05 g (0.11 mmol) of the compound obtained in 2.2 in 10 ml of methanol for 18 hours at reflux. After evaporating the solvent, the product is purified by chromatography on a column of silica gel by eluting with an ethyl acetate/heptane (¼) mixture. 0.02 g of the expected compound is obtained.

Yield=50%

EXAMPLE 5

5-(4'-Dimethoxymethyl-1,1'-biphenyl-2-yl)-2-triphenylmethyl-2H-tetrazole 0.285 g of magnesium in 4 ml of anhydrous tetrahydrofuran is introduced into a 2-necked, round-bottomed flask equipped with a reflux condenser and a dropping funnel. 2 g (8.6 mmol) of 1-bromo-4-(dimethoxymethyl)benzene in solution in 10 ml of anhydrous tetrahydrofuran are then added dropwise under gentle reflux. The mixture is left stirring for 1 hour at room temperature and then 11.6 ml of a 1M solution of zinc chloride in ethyl ether are added at 0° C. The mixture is left for 30 minutes at room temperature. The palladium complex is prepared in another round-bottomed flask by treating 0.205 g of dichlorobis(triphenylphosphine)palladium(II), dissolved in 10 ml of anhydrous tetrahydrofuran, with 0.6 ml of a 1M solution of diisobutylaluminium hydride in hexane. 3 g (5.8 mmol) of 5-(2-iodophenyl)-2-triphenylmethyl-2H-tetrazole in solution in 15 ml of anhydrous tetrahydrofuran are added to this solution. The mixture is stirred for 15 minutes at room temperature and the zinc derivative obtained above is introduced using a transfer needle. The mixture is stirred for 1 hour at room temperature. 15 ml of water are then added, the mixture is extracted with 100 ml of ethyl acetate, the extract is washed with 20 ml of a saturated sodium chloride solution and dried over magnesium sulphate.

The product obtained is purified by chromatography on a column of silica gel by eluting with an ethyl acetate/hexane (¼) mixture.

2.15 g of product are obtained in the form of a white solid.

Melting point=120°–121° C. Yield=68.47%

EXAMPLE 6

5-(4'-Dimethoxymethyl-1,1'-biphenyl-2-yl)-2-(1,1-dimethylethyl)-2H-tetrazole.

0.61 g of magnesium in 4 ml of anhydrous tetrahydrofuran is introduced into a 2-necked, round-bottomed flask equipped with a reflux condenser and a dropping funnel. 4.26 g (18.4 mmol) of 1-bromo-4-(dimethoxymethyl)benzene in solution in 15 ml of anhydrous tetrahydrofuran are then added dropwise under gentle reflux. The mixture is left to stir for 1 hour at room temperature and then 22 ml of a 1M solution of zinc chloride in ethyl ether are added at 0° C. The mixture is left for 30 minutes at room temperature.

The nickel complex is prepared in another round-bottomed flask by treating 0.33 g of dichlorobis(triphenylphosphine)nickel(II), dissolved in 10 ml of anhydrous tetrahydrofuran, with 0.35 ml of a 3M solution of methylmagnesium chloride in tetrahydrofuran. 3.28 g (10 mmol) of 5-(2-iodophenyl)-2-(1,1-dimethylethyl)-2H-tetrazole in solution in 15 ml of anhydrous tetrahydrofuran are then added. The mixture is stirred for 15 minutes at room temperature and the zinc derivative obtained above is then introduced using a transfer needle. The mixture is stirred for 1 hour at room temperature. 20 ml of water are then added, the mixture is extracted with 150 ml of ethyl acetate, the extract is washed with 20 ml of a saturated sodium chloride solution and dried over magnesium sulphate.

The product obtained is purified by chromatography on a column of silica gel by eluting with an ethyl acetate/hexane (¼) mixture.

2.46 g of product are obtained in the form of a white solid.

Melting point=59°–61° C. Yield=69.8%

EXAMPLE 7

2'-(1H-Tetrazol-5-yl)-1,1'-biphenyl-4-carboxaldehyde

METHOD NO. 1.

0.5 g (1 mmol) of the compound obtained in Example 3 is dissolved in 20 ml of methanol. 1 ml of acetic acid is added and the mixture is brought to reflux. The solvent is evaporated and the residue is taken up in 60 ml of 1N sodium hydroxide solution. The aqueous phase is extracted with 3×50 ml of ether. The aqueous phase is filtered and the filtrate is acidified to pH = 1 with concentrated hydrochloric acid. The precipitate is filtered and washed with water. 0.065 g of product is obtained in the form of a white powder.

Yield=25% Melting point=184°-186° C.

METHOD NO. 2

28 g (52 mmol) of the compound obtained in Example 5 are dissolved in a mixture of 200 ml of tetrahydrofuran and 70 ml of water. 70 ml of acetic acid are added and the mixture is brought to 50° C. for 4 hours. The solvents are evaporated and the residue is taken up in 200 ml of 1N sodium hydroxide solution. The aqueous phase is extracted with 3 times 250 ml of ethyl acetate and acidified to pH=1 with concentrated hydrochloric acid. The precipitate is filtered and washed with water.

8.9 g of product are obtained in the form of a white solid.

Yield=68% Melting point=183°-185° C.

The compounds according to the invention are particularly useful for the preparation of various heterocyclic derivatives which are substituted by a 2'-(tetrazol-5-yl)-1,1'-biphenyl-4-methylenyl group, such as, for example, the 3-pyrazolone and 4-pyrimidinone derivatives described respectively in French Patent Application FR 91 02031 and European Patent Application EP 0500409.

The synthesis is described in Scheme 3 below:

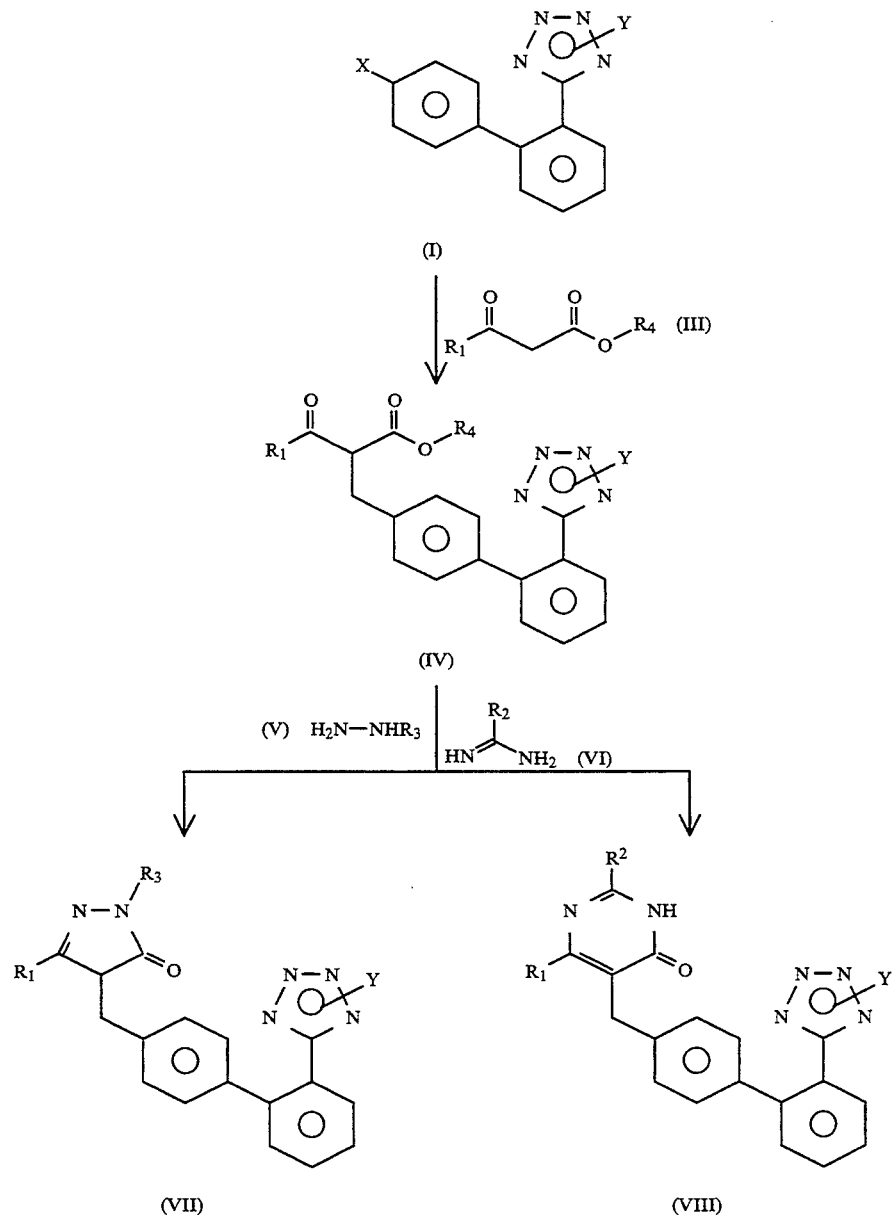

A compound of formula (I), in which X and Y are as defined above, is condensed with a β-ketoester derivative of formula (III) and a hydrogenation is carried out under conditions which are well known in organic chemistry, conditions described, for example, in *Org. React.*, 1967, 15, 202, to prepare β-ketoester derivatives of formula (IV), derivatives described, inter alia, in French Patent Application FR 91 02031 and in European Patent Application EP 0500409. These compounds are reacted, either with hydrazines of formula (V) or with amidines of formula (VI), in order to prepare 3-pyrazolone derivatives of formula (VII) or 4-pyrimidinone derivatives of formula (VIII), respectively, as is described in French Patent Application FR 91 02031 and European Patent Application EP 0500409.

The example below illustrates the synthesis of a compound of formula (IV), a compound converted to a compound of formula (VII) or (VIII) according to Scheme 3 on the previous page.

Synthesis of methyl 3-oxo-2-[[2'-(2-(1,1-dimethylethyl)-2H-tetrazol-5-yl)-1,1'-biphenyl-4-yl]methyl]heptanoate.

3.6 g (12 mmol) of the compound described in Example 4 are dissolved in 25 ml of toluene. 1.96 g (12 mmol) of methyl 3-oxoheptanoate, 175 mg (3 mmol) of acetic acid and 50 mg (0.5 mmol) of piperidine are added. The mixture is brought to reflux with azeotropic separation for 2 hours. 5 ml of solvent are removed and the mixture is put back on reflux for 5 hours. 1 ml of a solution containing 1.2 g (20 mmol) of acetic acid and 0.35 g (4 mmol) of piperidine in 5 ml of toluene is added and the mixture is brought to reflux for 5 hours. The solvent is evaporated and the crude reaction product is taken up in 80 ml of ether. This solution is washed with 40 ml of hydrochloric acid, then with 2×40 ml of 1M sodium carbonate and with 40 ml of water. The organic phase is dried over magnesium sulphate. After evaporating the solvent, 4.9 g of product are obtained in the form of a yellow oil. The oil obtained is taken up in 80 ml of methanol, 350 mg of palladium-on-charcoal are added and the mixture is hydrogenated on a Parr apparatus for 3 hours. The catalyst is filtered off and the solvent is evaporated. The crude reaction product is purified by chromatography on a column of silica gel by eluting with an ethyl acetate and heptane gradient. 3.6 g of a pale-yellow oil are obtained.

Yield=69% $^1$H NMR (CDCl$_3$, δ in ppm with respect to TMS): 8.00–7.92, m, 1H, aromatic; 7.64–7.43, m, 3H, aromatic; 7.15, s, 4H, aromatic; 3.79, t, 1H, 7.7 Hz, >CH—; 3.69, s, 3H, OMe; 3.15, d, 2H, 7.7 Hz, CH$_2$—Ar; 2.64–2.25, m, 2H, CH$_2$—C(O); 1.59, s, 9H, (CH$_3$)$_3$; 1.62–1.41, m, 2H, CH$_2$; 1.36–1.15, m, 2H, CH$_2$; 0.87, t, 3H, CH$_3$. IR (NaCl, film): 1750, 1720 cm$^{-1}$ In the formulae (III) to (VIII), R$_1$ represents either a straight or branched (C$_{1-7}$)alkyl group, or a straight or branched (C$_{3-9}$)alkenyl group or a cyclo(C$_{3-7}$)alkyl(C$_{1-6}$)alkyl group, R$_2$ represents either a hydrogen atom, or a straight or branched (C$_{1-7}$)alkyl group, or a straight or branched (C$_{3-9}$)alkenyl group, or a straight or branched (C$_{3-9}$)alkynyl group, or a straight or branched (C$_{1-7}$)alkoxy group, or a cyclo(C$_{3-7}$)alkyl(C$_{1-3}$)alkyl group, or a cyclo(C$_{3-7}$)alkoxy group, or a straight or branched (C$_{1-7}$)alkylthio group, or a cyclo(C$_{3-7}$)alkylthio group, or an optionally substituted aryl group, or an optionally substituted aryloxy group, or an optionally substituted arylthio group, or an aryl(C$_{1-3}$)alkyl group optionally substituted on the ring, or an aryloxy(C$_{1-3}$)alkyl group optionally substituted on the ring, or an arylthio(C$_{1-3}$)alkyl group optionally substituted on the ring or a heteroaryl(C$_{1-3}$)alkyl group optionally substituted on the ring, R$_3$ represents either a hydrogen atom, or a straight or branched (C$_{1-7}$)alkyl group, or a straight or branched (C$_{3-9}$)alkenyl group, or a straight or branched (C$_{3-9}$)alkynyl group, or an optionally substituted aryl group, or an aryl(C$_{1-3}$)alkyl group optionally substituted on the ring, or an aryloxy(C$_{1-3}$)alkyl group optionally substituted on the ring, or an arylthio(C$_{1-3}$)alkyl group optionally substituted on the ring, or a cyclo(C$_{3-7}$)alkyl(C$_{1-3}$)alkyl group, or a heteroaryl(C$_{1-3}$)alkyl group optionally substituted on the ring, R$_4$ represents either a methyl group, or an ethyl group, or a 1,1-dimethylethyl group, or a phenylmethyl group.

We claim:

1. A compound of the general formula (I)

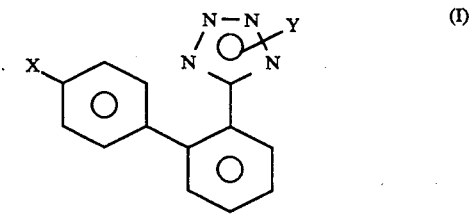

in which X represents a group selected from dibromomethyl, formyl, (C$_{1-4}$)alkyl, a group CH(OR$_5$)$_2$ and a group CH(OH)OR$_5$, wherein the or each R$_5$ is selected from hydrogen and (C$_{1-3}$)alkyl or the two R$_5$'s in the case of CH(OR$_5$)$_3$ are linked to provide a heterocyclic ring selected from 1,3-dioxolane and 1,3-dioxane, and Y represents an atom or group selected from hydrogen, 1,1-dimethylethyl, triphenylmethyl and a group CH$_2$OR$_6$, wherein R$_6$ is a group selected from methyl, phenylmethyl, 1,1-dimethylethyl, 2,2,2-trichloroethyl, benzyloxycarbonyl and 2,2,2-trichloroethyloxycarbonyl, Y being in position 1 or 2 on the tetrazole ring.

2. A compound according to claim 1, wherein X represents a group selected from dibromomethyl, formyl, dimethoxymethyl, 1,3-dioxolan-2-yl and 1,3-dioxan-2-yl, and Y represents an atom or group selected from hydrogen, 1,1-dimethylethyl, triphenylmethyl and methoxymethyl.

3. A compound according to claim 2, wherein X represents a group selected from dibromomethyl and formyl and Y represents an atom or group selected from hydrogen, 1,1-dimethylethyl and triphenylmethyl.

4. 5-(4'-Dibromomethyl-1,1'-biphenyl-2-yl)-2-triphenylmethyl-2H-tetrazole.

5. 5-(4'-Dibromomethyl-1,1'-biphenyl-2-yl)-2-(1,1-dimethylethyl)-2H-tetrazole.

6. 2'-(2-Triphenylmethyl-2H-tetrazol-5-yl)-1,1-biphenyl-4-carboxaldehyde.

7. 2'-[2'-(1,1-Dimethylethyl)-2H-tetrazol-5-yl]-1,1'-biphenyl-4-carboxaldehyde.

8. 5-(4'-Dimethoxymethyl-1,1'-biphenyl-2-yl)-2-triphenylmethyl-2H-tetrazole.

9. 5-(4'-Dimethoxymethyl-1,1'-biphenyl-2-yl)-2-(1,1-dimethylethyl)-2H-tetrazole.

10. 2'-(1H-Tetrazol-5-yl)-1,1'-biphenyl-4-carboxaldehyde.

11. A process for the preparation of a compound of formula (Ia)

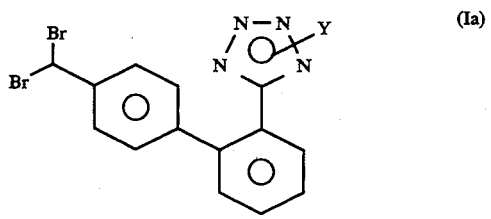

wherein Y is an atom or group selected from hydrogen, 1,1-dimethylethyl, triphenylmethyl and a group CH$_2$OR$_6$, wherein R$_6$ is a group selected from methyl, phenylmethyl, 1,1-dimethylethyl, 2,2,2-trichloroethyl, benzyloxycarbonyl and 2,2,2-trichloroethyloxycarbonyl, Y being in position 1 or 2 on the tetrazole ring, which process comprises reacting a compound of formula (II)

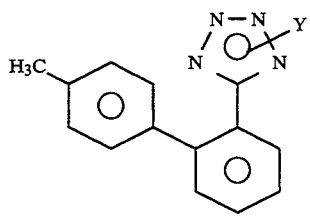
(II)

with N-bromosuccinimide under free-radical reaction conditions.

12. The process of claim 11 further comprising subjecting the compound of formula (Ia) to a hydrolysis reaction to prepare a compound of formula (Ib)

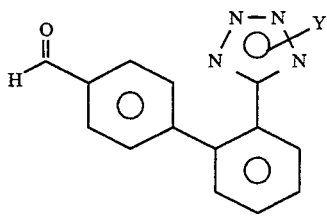
(Ib)

13. The process of claim 12 further comprising protecting the aldehyde functional group of the compound of formula (Ib) in the acetal form to prepare a compound of formula (Ic)

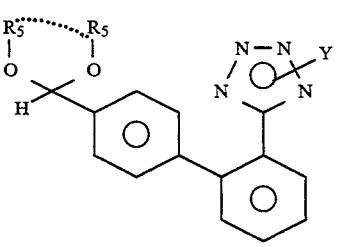
(Ic)

* * * * *